United States Patent [19]
Litz et al.

[11] 3,985,507
[45] Oct. 12, 1976

[54] AUTOMATIC TEST SAMPLE HANDLING SYSTEM

[75] Inventors: Frank A. Litz, Hopewell Junction; Einar S. Mathisen, Poughkeepsie; Paul A. Schumann, Jr., Wappingers Falls; Carl R. Valentino, Hopewell Junction, all of N.Y.

[73] Assignee: International Business Machines Corporation, Armonk, N.Y.

[22] Filed: Sept. 5, 1975

[21] Appl. No.: 610,701

[52] U.S. Cl. .............................. 23/253 R; 141/170; 214/310; 356/244
[51] Int. Cl.² .................. B65B 43/42; B65G 65/02; G01N 1/10; G01N 21/24
[58] Field of Search............ 23/253 R, 259; 356/96, 356/180, 184, 185, 244, 246; 141/170; 214/309, 310

[56] References Cited
UNITED STATES PATENTS

| | | |
|---|---|---|
| 2,799,414 | 7/1957 | Streckfuss........................... 214/309 |
| 3,687,632 | 8/1972 | Natelson ....................... 23/253 R X |
| 3,704,953 | 12/1972 | Carter et al................... 23/253 R X |
| 3,917,455 | 11/1975 | Bak et al........................... 23/259 X |

*Primary Examiner*—Robert M. Reese
*Attorney, Agent, or Firm*—Douglas R. McKechnie

[57] ABSTRACT

An automatic handling system selectively conveys test samples to a test probe for analysis by an instrument. The test samples are contained in sample containers. A magazine contains sampler holders each of which contains sample containers. A transport system conveys the magazine so that the holders successively pass through an extraction station from where the holders can be taken from the magazine and placed back therein. The holders upon extraction are then conveyed past a test probe so that individual samples can be selectively presented to the probe.

10 Claims, 2 Drawing Figures

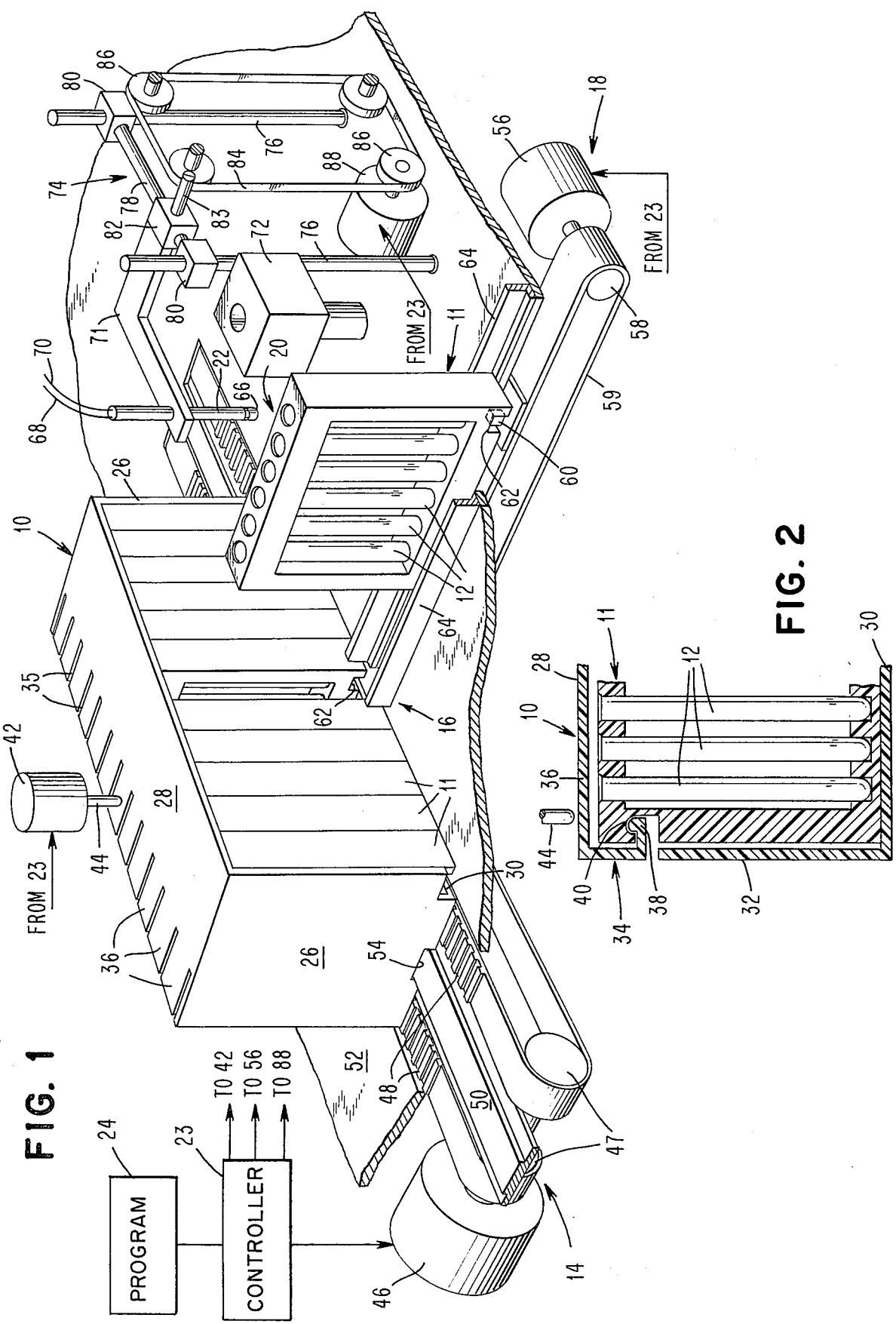

AUTOMATIC TEST SAMPLE HANDLING SYSTEM

BACKGROUND OF THE INVENTION

1. Field of the Invention

This invention relates to an automatic test sample handling system. More particularly, it relates to a system in which a plurality of test samples are automatically and selectively presented to a test probe for analysis by an instrument connected to the probe.

2. Prior Art

There currently exists a wide variety of analytical instruments that use test probes for detecting some characteristic associated with a test sample and providing an electrical analog signal proportional to the characteristic. A specific example is a spectrophotometer having a fiber optic light system designed to project light onto or through a sample and measure the reflectance or transmittance thereof across a spectrum of different or discrete wavelengths.

In the past, many such instruments were designed to have an individual test sample manually prepared and handled so as to be presented to the test probe. More recently, there has been a trend to providing automatic sample handling systems which are capable of handling a plurality or multiplicity of test samples in which the samples have been previously prepared for analysis. In such systems, the automatic sample handling allows the various tests to be made at a relatively high throughput rate. Some of these systems include some form of a program controlled digital electronic controller that controls the operation of a transport mechanism having some form of stepping motors that selectively move the samples through the test station.

While such instruments are capable of testing a wide variety of materials, the instruments find multiple applications for analyzing liquid samples in which the sample is contained within a test tube. Generally, testing procedures associated with such liquid samples involve two phases, the sample preparation phase and the actual testing. A more specific example to illustrate both phases deals with the use of colorimetric reagents to detect or measure the concentration of a substance within the liquid. Here, the sample preparation includes adding the reagent to the sample. After the reagent has sufficient time to react with the sample and reach a stable level, the resultant test sample is then analyzed by a spectrophotometer to determine the color characteristics thereof. These color characteristics are proportional to the concentration of the substance being analyzed. Analyses and tests of this nature are well known and described within the current literature. See for example, "Instrumental Methods of Analysis", Fifth Edition, by H. H. Willard et al, published by D. VanNostrand Co., New York. An example of an automatic spectrophotometric sample system is disclosed in U.S. Pat. No. 3,704,953 — Carter et al. Examples of automatic test tube transport or handling systems are disclosed in U.S. Pat. Nos. 3,687,632 — Natelson and 3,768,526 - Sanz et al.

SUMMARY OF THE INVENTION

In connection with an automatic sample handling system, there are several desirable features which the subject invention is designed to provide. One of the objects of the invention is to provide a basic test sampling handling system for selectively positioning a test sample or material at a work station for either sample preparation or testing and analysis.

Another object of the invention is to provide a basic test sample handling system that can be used with different test probes with either no or little modification to accomodate different type probes and test procedures.

Still another object of the invention is to provide an automatic test sample handling system that is operable under program control to selectively present one out of many test samples to a test station for analysis at a given time.

A further object of the invention is to provide a handling system having a high throughput rate in which the samples are placed in a magazine or rack and from which an individual test sample can be selected.

Briefly, the manner in which these and other objects and advantages of the invention are achieved is to provide a magazine that holds a plurality of sample holders each of which holds a plurality of containers for the samples to be analyzed. The magazine is transported along a predetermined path under program control so as to selectively present the holders to an extraction station at which a holder may be taken from and later placed back into the magazine. A second transport mechanism extracts the holder from the magazine and conveys it along a predetermined path to a work station or test station, under program control, so as to allow preselected one or ones of the samples to be worked upon.

These and other objects, features and advantages of the invention will be apparent from the following more particular description of a preferred embodiment of the invention as illustrated in the accompanying drawing.

BRIEF DESCRIPTION OF THE DRAWING

FIG. 1 is a perspective view with portions broken away, some portions in section and some portions schematically shown, of an automatic sample handling system embodying the invention; and FIG. 2 is a sectional view with portions removed of a detail of the apparatus shown in FIG. 1.

GENERAL DESCRIPTION

Referring now to the drawing, the embodiment of the invention shown in FIG. 1 generally comprises a magazine 10 for holding a plurality of sample or test tube holders 11 each one of which holds or supports a plurality of test tubes 12. A first transport or conveying means 14 is designed to move magazine 10 in a predetermined orientation along a first path that extends through an extraction station 16 from which a holder 11 positioned thereat can be removed or extracted from magazine 10 and placed back therein. A second transport or conveying means 18 is operable to selectively move a holder 11 from magazine 10 and selectively present a test tube 12 contained therein to work or test station 20 at which a test probe 22 can be inserted into such test tube 12 in a manner described in detail below. A controller 23 operates under the control of a program 24 to provide signals for operating the motors and electromagnet in the manner described in detail below.

In the general operations of the system, the transport means 14 moves magazine 10 until the desired holder is located at extraction station 16. Then, the transport means 18 is actuated to remove the holder 11 from magazine 10 until the desired test tube is at test station 20. The probe 22 is then moved so as to be immersed in the liquid in the aligned test tube after which the measurements can be taken. Thereafter, the probe is withdrawn and the transport means can be actuated so as to align another test tube in the same holder or to replace the holder in magazine 10 and select another one.

DETAILED DESCRIPTION

Magazine 10 is in the form of a five sided shell or box that is open at one side to receive holders 11. Magazine 10 comprises flat end walls 26, top and bottom walls 28 and 30 and back wall 32. Magazine 10 is designed to hold a predetermined number of holders 11. Quite obviously, different size magazines can be used to accomodate different size holders and the holder in any given magazine may differ from those in other magazines.

A releasable detent means 34 is formed between magazine 10 and each of holders 11. This is done by providing a series of slots 35 that divide the left upper edge (as viewed in FIG. 1) of magazine 10 into a series of flexible cantilevers 36 the lower edge of which is formed into a detent arm 38 that cooperates with a detent pocket 40 formed in the rear of a holder 11. When a holder is positioned in magazine 10, the detent arm 38 and pocket 40 are engaged so as to provide an interlock tending to prevent removal of the holder. The shape of the pocket and arm can be such as to provide a positive interlock, or it may be one which requires a predetermined force to overcome the release mechanism. Various other detents may be formed such as merely placing a magnet in each of the holders engageable with a plate on the inside of the magazine so that only the force of the magnetic attraction need be overcome. The detent means facilitates handling a loaded magazine by preventing holders 11 from sliding out of the magazine should it be tipped or tilted.

As shown in the drawing, an electromagnet 42 is positioned over the path of travel of magazine 10 in alignment with extraction station 16. Magnet 42 has a plunger 44 which when the electromagnet 42 is actuated, moves downwardly a fixed distance so as to depress the cantilever 36 beneath it causing it to move downwardly and thereby disengage the detent 38 and pocket 40 allowing the holder to be readily withdrawn. Once the holder is withdrawn, the electromagnet can be de-energized and preferably, when the holder is pushed back into the magazine by transport means 18, the detent arm and pocket will be mechanically reengaged. It should be noted however that dependent upon the shape of the detent mechanism, it might be necessary to re-energize electromagnet 42 so that the detent means can be re-engaged.

Transport means 14 comprises a conventional reversible stepping motor 46 actuated by appropriate pulses from controller 23 to drive a pair of pulleys 47 so as to drive belts 48 having teeth thereon engageable with suitable teeth (not shown) formed in the bottom wall of magazine 10. A slide plate 50 is attached to a bed plate 52 and in engageable with a slot 54 in the bottom of magazine 10 so as to define a fixed path along which magazine travels under the control of transport means 14. In order for program 24 to control movement of magazine 10, the positions of the magazine has to be known or detectable. Thus, some form of a detector could be used or the belts 48 and magazine 10 could be shaped so that the magazine occupies a predetermined or known position relative thereto. Motor 46 is operable to move magazine 10 in either direction along the fixed path.

Transport means 18 comprises a reversible stepping motor 56 that operates under the control of signals from controller 23 so as to drive a pully 58 and belt 59. Attached to belt 59 is an upstanding member or stud 60 that is designed to be received in a slot 62 in holder 11. When thus engaged, operation of motor 56 causes the holder 11 engaged with stud 60 to be moved along a second path that extends perpendicular to the path of movement of magazine 10. A pair of guide tracks 64 are aligned with work station 16 so that as a holder is withdrawn from magazine 10, the holder slides along tracks 64. Stud 60 is movable from an extraction position wherein it is located at extraction station 16 so as to pass through the slots 62 of holders 11 as the magazine is moved along with first path. When the predetermined holder 11 is positioned at station 16, motor 56 can then be actuated causing stud 60 to pull the holder from the magazine and position the selected one of the test tubes therein beneath or at test station 20. Reverse operation of motor 56 causes the holder to be moved towards and into the magazine.

Probe 22 is a fiber optic type having a reflecting mirror 66 spaced a fixed distance beneath the ends of a pair of fiber optic bundles 68 and 70. Light from the instrument is passed along bundle 68 and reflected off of mirror 66 into the lower ends of bundle 70 where it is conducted back to a sensing or transducing element of the instrument. Probe 22 is movable from a position immersed in a test tube for analyzing the contents thereof to another position in a wash device 72 which cleanses the probe between measurements. To accomplish this movement, a probe support mechanism 74 is provided in which probe 22 is supported on an arm 71. A pair of upright rods 76 are mounted on bed plate 52. A crossrod 78 is attached at its ends to slides 80 which are slidably engaged with rods 76. Probe support arm 71 is attached to a slide 82 slidably mounted on crossrod 78. A pin 83 is connected to slide 82 and is attached to a belt 84 supported by a pulley system or series of pulleys 86. A stepping motor 88 drives one of pulleys 86 so as to move belt 84 and pin 83. Pulleys 86 are positioned so as to define a path of travel for pin 83 that causes the probe to move, as previously indicated, between positions immersed in either an aligned test tube or the wash device 72. During such movement, the slides 80 allow for the vertical component while slide 82 allows for the horizontal component of movement of pin 83 to be translated into a corresponding movement of probe 22.

It should be noted that because of the reversible nature of the transport mechanisms, the test tubes do not have to be positioned sequentially at the test station. The tubes can be positioned randomly. This allows, e.g., a measurement to be taken on the contents of one tube at one time, subsequent measurements to be taken on others, and then a later measurement to be taken or repeated on the contents of the one tube.

It should be apparent with the handling system thus far described that many modifications and changes can be made in the details without departing from the scope of the invention. The invention resides in the general combination, as defined in the claims, and not in the details of the elements which details can be varied by using other known conventional elements and mechanisms. One modification would be to elongate the length of transport means 14 so that more than one magazine could be placed thereon. Another would be to elongate transport means 18 and provide additional extracting mechanisms and additional test or work stations so more than one holder might be worked on at a given time. Other forms of probes might be used, such as a stationary one mounted along the path to project light through a sample holder at the test station. The test tubes themselves could be removed from the holders. Instead of a test probe, some form of a sample preparation device could be used, such as a dispensor for reagents, so that the mechanism is used for sample preparation purposes instead of sample testing. It should also be apparent that different size sample holders and test tubes can readily be used where the different sizes are taken into account within the program 24 that controls operation of the system. The system may also include details disclosed and claimed in application Ser. number 610,723, filed concurrently herewith, for "Sample Handling System" by Thomas C. Nielsen et al and assigned to the assignee hereof.

Although the invention has been shown and described with respect to a single advantageous embodiment thereof, it should be understood by those skilled in the art that various changes in form and detail may be made therein, in addition to those described above, without departing from the spirit and scope of the invention, which is to be limited only as set forth in the following claims.

What is claimed is:

1. A handling system for storing, conveying and presenting a plurality of samples, contained in sample containers, to a work station comprising:
   a magazine;
   first conveying means for moving said magazine along a first path, said magazine having a predetermined orientation relative to such path;
   a plurality of holders carried by said magazine and being removable therefrom along a line of movement predetermined relative to said orientation;
   a plurality of said sample containers carried by each of said holders;
   said work station being spaced from said first path;
   and second conveying means intersecting said first path and extending adjacent to said work station;
   said first conveying means being operative to locate said holders one-at-a-time at said intersection;
   said second conveying means being operative to remove a holder, located at said intersection, from said magazine and transport such holder past said work station so as to selectively locate a predetermined sample container therein.

2. The combination of claim 1 wherein said second conveying means comprises:
   a selectively operable motor;
   and an actuator driven by said motor and engageable with said holders;
   each of said holders comprises means engageable with said actuator for selectively moving said holders in response to operation of said motor.

3. The combination of claim 1 comprising:
   detent means between said holder and said magazine releasably detaining said holders against movement out of said magazine.

4. In a system for handling a plurality of test samples contained in test tubes which system comprises a controller operative under program control to selectively move predetermined test samples to a test station for analysis of such samples, the combination comprising:
   a box-like magazine open at one side;
   a plurality of holders carried by said magazine and being removable therefrom and replaceable therein through said one side;
   a plurality of said test tubes carried by each of said holders;
   first transport means for successively conveying said magazine past an extraction station and comprising a first motor selectively operable under signals from said controller to position a predetermined one of said holders containing a predetermined one of said test tubes at said extraction station;
   and second transport means for extracting a holder from said magazine at said extraction station, moving such holder to said test station and replacing such holder in said magazine and including a second motor selective operable in response to signals from said controller to position said predetermined one of said test tubes at said test station.

5. The combination of claim 4 comprising:
   a test probe at said test station, said test probe being operative to receive electromagnetic radiation from a test sample in said predetermined test tube.

6. The combination of claim 5 comprising:
   movable support means for said test probe;
   and motive means operable in response to signals from said controller for moving said support means and said test probe between a first position in said test station and a second position displaced from said first position.

7. The combination of claim 4 wherein:
   said first transport means conveys said magazine along a linear first path of movement;
   and said second transport means moves a holder extracted from said magazine along a second path of movement extending perpendicular to said first path.

8. The combination of claim 7 comprising:
   detent means on said magazine and said holders releaseably restraining said holders against movement out of said one side of said magazine.

9. The combination of claim 7 wherein:
   said second transport means comprises an actuator movable in response to operation of said second motor, said actuator being engageable with said predetermined holder for moving it along said second path.

10. The combination of claim 7 wherein each of said motors is reversible whereby said magazine and one of said holders is selectively moveable along said first and second paths in either of forward and reverse directions so as to permit random positioning of a test tube at said test station.

* * * * *